United States Patent
Wood, Sr.

[11] Patent Number: 5,331,950
[45] Date of Patent: Jul. 26, 1994

[54] VIDEO LAPAROSCOPE WITH HIGH-ILLUMINANCE LOW-WATTAGE LIGHT SOURCE

[75] Inventor: Robert J. Wood, Sr., Syracuse, N.Y.

[73] Assignee: Welch Allyn, Inc., Skaneateles Falls, N.Y.

[21] Appl. No.: 780,762

[22] Filed: Oct. 22, 1991

[51] Int. Cl.⁵ ............................................. A61B 1/06
[52] U.S. Cl. ....................................... 128/6; 313/634
[58] Field of Search .............. 128/6, 4; 313/634, 571; 358/98

[56] References Cited

U.S. PATENT DOCUMENTS

| | | | |
|---|---|---|---|
| 4,729,018 | 3/1988 | Watanabe et al. | 128/6 X |
| 4,800,424 | 1/1989 | Noguchi | 128/6 X |
| 4,821,116 | 4/1989 | Nagasaki et al. | 128/4 X |
| 4,866,516 | 9/1989 | Hibino et al. | 128/6 X |
| 4,872,740 | 10/1989 | Terada et al. | 128/7 X |
| 4,878,112 | 10/1989 | Ieoka | 128/6 X |
| 4,878,485 | 11/1989 | Adair | |
| 4,887,154 | 12/1989 | Wawro et al. | 128/6 X |
| 4,941,456 | 7/1990 | Wood et al. | 128/6 |
| 5,117,154 | 5/1992 | Thomas et al. | 313/634 |
| 5,144,201 | 9/1992 | Graham et al. | 313/634 |
| 5,184,044 | 2/1993 | Thomas | 313/638 |

FOREIGN PATENT DOCUMENTS

| | | | |
|---|---|---|---|
| 2746614 | 4/1979 | Fed. Rep. of Germany | 128/6 |
| 2943207 | 4/1981 | Fed. Rep. of Germany | 128/6 |
| 9203104 | 3/1992 | PCT Int'l Appl. | |

OTHER PUBLICATIONS

Avco, "Fiberay Surgical Illumination System", Aug. 1978.

Primary Examiner—Richard J. Apley
Assistant Examiner—Karen A. Jalbert
Attorney, Agent, or Firm—Harris Beach & Wilcox

[57] ABSTRACT

A laparoscope assembly has a miniature video camera mounted either proximally or distally in its insertion tube and has an optical fiber bundle that extends to the distal end of the insertion tube from a light source which can be incorporated in a video processor. The light source can be formed of one or more low-wattage metal halide discharge lamps (i.e., 20 watts) with an ellipsoidal reflector to concentrate the visible light from the lamp onto the proximal end of the optical fiber bundle. The lamp produces balanced white visible light but very little infrared.

5 Claims, 3 Drawing Sheets

VIDEO LAPAROSCOPE WITH HIGH-ILLUMINANCE LOW-WATTAGE LIGHT SOURCE

BACKGROUND OF THE INVENTION

This invention relates to borescopes or endoscopes of the type in which a miniature video camera is mounted at a distal viewing head of an elongated insertion tube. The invention is more particularly concerned with an improved laparoscope in which illumination for the miniature video camera is supplied from a low-wattage but high-efficiency lamp and thence through a light conduit to the tip of the laparoscope probe tube.

Recently, interest has increased in the use of video instruments for surgical applications to permit a surgeon to carry out a procedure with minimal intervention in the patient. An example of one such video instrument is a laparoscope for performing surgery in the abdominal cavity, where the instrument is inserted through a small incision. Other probes are provided for diagnosis of medical conditions in the colon or in the gastro-enteric tract. Small probes can also be used in eye surgery. Further examples are found in industrial probes, i.e., borescopes, for inspection of equipment such as boilers or steam generators, or jet engine rotors where non-destructive penetration of the equipment is necessary. In each case the tissues or parts to be investigated may be quite sensitive to heat; thus if infrared or heat is produced with the light from the instrument's light box, inspection can injure or damage the target.

It is also desirable for laparoscopes to operate at low power consumption rates, for example, so that the unit can be constructed compactly and of light weight, and also so that the laparoscope can be made battery powered and portable, e.g. for veterinary purposes.

However, until now suitable illumination was possible only with high wattage, high pressure xenon arc lamps. These produce a large amount of waste heat and their energy can not be focussed down onto a small spot to enter the fiber optic bundle or other light conduit.

A number of full-color video probes of this general type have been described, for example, in Danna et al. U.S. Pat. No. 4,491,865, Danna et al. U.S. Pat. No. 4,539,586, and Longacre et al. U.S. Pat. No. 4,523,224.

OBJECT SUMMARY OF THE INVENTION

It is an object of this invention to provide an improved laparoscope that avoids the problems of the prior art.

It is another object to provide a laparoscope which has a light source that produces white light in fairly balanced intensities of its composite primary colors but only a minimal amount of infrared, i.e., radiant heat, so that there is much reduced danger of tissue damage from heating.

It is a further object to produce a laparoscope which operates efficiently at low power, so that the probe can be made of extremely small diameter.

In accordance with an aspect of this invention a laparoscope or other similar probe has a miniature video camera that incorporates a miniature electronic imager and a lens assembly which are disposed either at the distal tip or at a proximal end of an insertion tube. For insertion tubes of about 5 mm or larger, the camera can be distally mounted. For very slim insertion tubes, the camera can be proximally mounted, with a relay lens system being contained in the insertion tube. The insertion tube can be rigid or can have its tip portion articulatable.

The small video camera can be incorporated in an add-on camera attachment for laparoscopes having a proximal viewing port.

Disposing the camera at the distal tip of the laparoscope insertion tube reduces the amount of focussing and relay lenses to be carried in the tube. This means less light is lost in the lens system, so the needed amount of illumination optical fiber bundle is reduced which also permits the insertion tube to be made smaller.

The insertion tube proximal end is coupled through a flexible cable or umbilical to a connector module that plugs into a socket in a video processor unit. A video cable that extends through the insertion tube and umbilical has terminals in the connector module that supply the video signal from the miniature camera to electronic circuitry in the processor, which supplies a suitable signal to a full color or monochrome monitor. An image of a target area, such as a tissue within a patient's body cavity, can be viewed on the monitor.

Also within the processor is a high illuminance, but low-wattage light source in the form of one or more metal halide discharge lamps. These can preferably be of the type described in Copending patent application Ser. Nos. 07/484,166, filed Feb. 23, 1990; 07/636,742, 07/636,743 and 07/636,744, each filed Dec. 31, 1990, and which have an assignee common herewith. The lamp typically operates at a power of about 20 watts dc, and has an efficacy of 35 lumens per watt or more. The quality of light produced, which can be controlled by the selection of salts employed, the dosage of mercury, and mechanical structure, has an emission spectrum in the visible band, with very little radiation produced in the infrared band. Also, the arc gap of this lamp is small, which produces a small spot of light when focused onto the fiber optic bundle used for illumination. The small spot size allows almost all the light energy to be directed into the proximal end of a very small fiber bundle. The smaller illumination bundle permits the insertion tube to be made much smaller than was previously possible while still delivering plenty of light to the target area. Also, because small optical fiber bundles can be used, the probe can incorporate redundant optical fiber bundles, which can each be associated with a respective light source. Also, because the lamp operates at low power (e.g. 20 watts), producing limited infrared radiation, and with virtually all the light being focused onto the fiber optic bundle, the light source can be made much more compact, and the lamp power supply can be much smaller. The light incident on the target consists substantially only of visible light, with very little radiant heat. This permits the operator to view and examine tissues for extended intervals without danger of tissue damage.

The above and many other objects, features, and advantages of this invention will become apparent to those skilled in this art from the ensuring description of an embodiment of this invention, in conjunction with the accompanying Drawing.

DETAILED DESCRIPTION OF A PREFERRED EMBODIMENT

Figure 1:
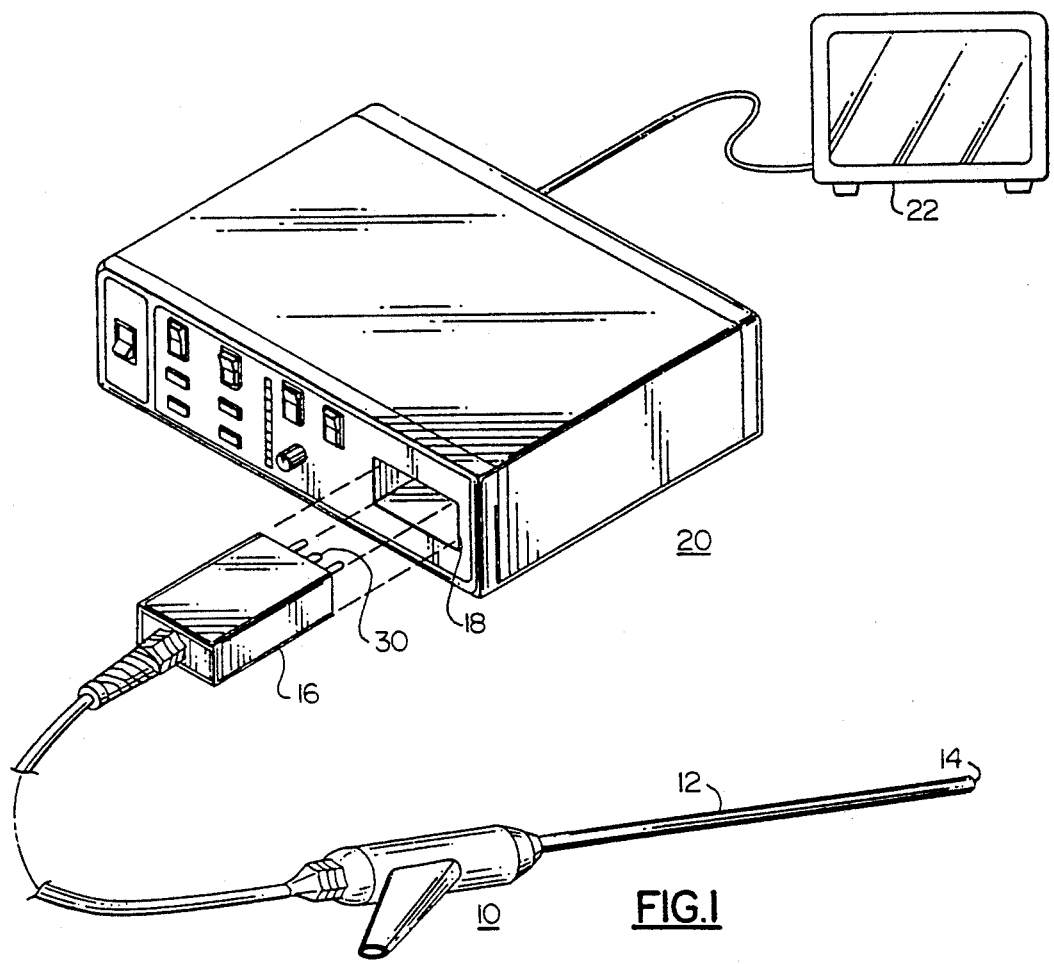
FIG. 1 is a perspective view of a laparoscope according to one embodiment of this invention.

With reference to the Drawing, and initially to FIG. 1, a laparoscope 10 according to an embodiment of the present invention has an elongated, narrow insertion tube 12 with a distal tip 14 at which a camera is disposed. The tube 12 can be entirely rigid or can be rigid with the distal tip 14 being articulatable (i.e., Rigi-flex). Wires, cables, and fiber optic bundle or bundles pass from the distal tip 14 through the tube 12 and then through a flexible umbilical 15 to a connector module 16 that plugs into a socket 18 of an electronic video processor unit 20. The video signal received from the camera is processed by electronic circuitry in the processor unit 20, which furnishes a suitable video signal to a color monitor 22. Synchronizing signals are also produced in the processor unit and are fed forward through the insertion tube to the camera. Also, an electronic package in the connector module 16 processes the video signal from the camera so that the video levels match the circuitry within the processor unit 20.

Figure 2:
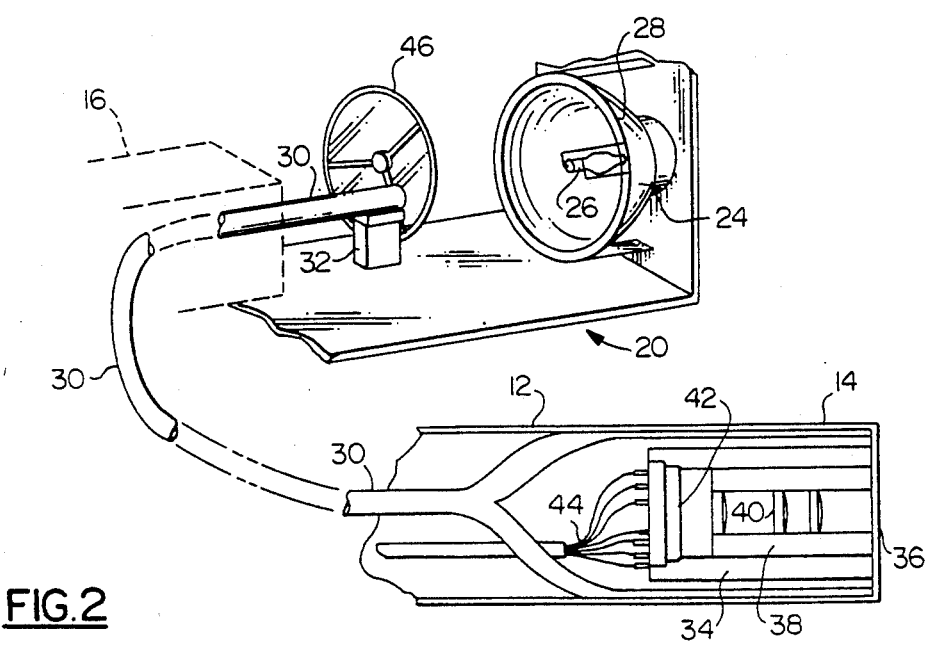
FIG. 2 is a cutaway partial view of salient portions of the laparoscope of FIG. 1.
Figure 3:
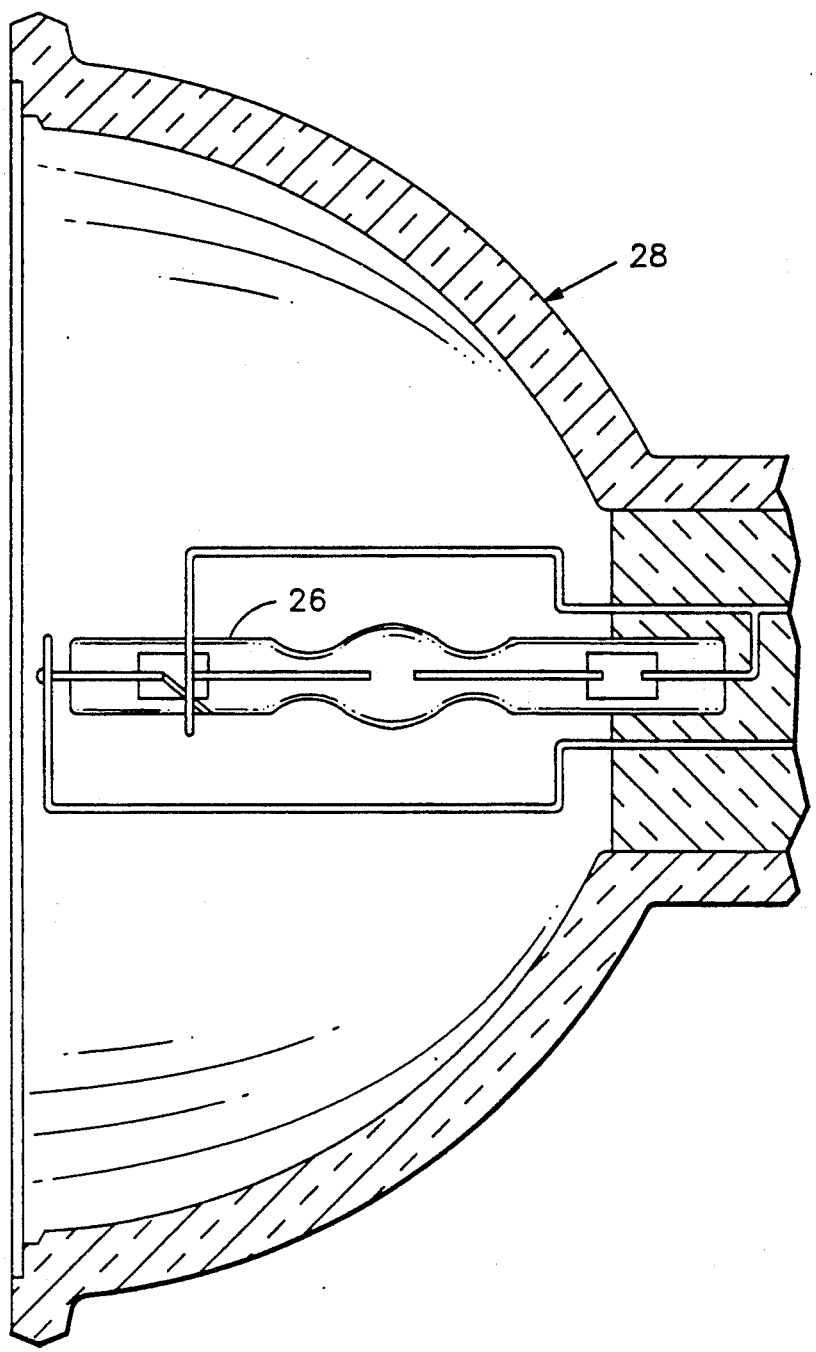
FIG. 3 is a more detailed sectional view of the lamp and associated reflector employed in the laparoscope of FIG. 1.

As shown schematically in FIG. 2, the processor unit 20 contains a light source 24 which is comprised of a small metal halide arc lamp 26 and an associated ellipsoidal reflector 28. The lamp 26 is of the type described in Copending patent application Ser. No. 07/484,166 and has a power draw of 50 watts or less, here 20 watts dc. The lamp has a point source characteristic and has an emission spectrum that is substantially entirely in the visible band, i.e., producing only very small quantities of infrared radiation. The lamp 26 is filled with an appropriate dose of mercury and salt so as to produce white light, i.e. fairly balanced intensities of red, green, and blue wavelengths. The reflector 28 (shown in cross section in FIG. 3) is of the ellipsoidal type. The lamp 26 is mounted so that its arc is disposed at one focus of the reflector 28 and with a proximal end of a fiber optic bundle 30 is situated at a second focus of the reflector 28. This concentrates the light of the lamp 26 onto a small spot which corresponds to the size of the lamp's discharge arc. Because the arc length, i.e., the gap between anode and cathode, is small, the spot at the second focus is very small, e.g. 0.1 inch or less, as compared with a minimum spot size of 0.3 to 0.4 inches that can be obtained with typical, prior-art 250 watt (or higher power) metal halide arc lamps that are commonly used.

As also shown in FIG. 2, a proximal end of the fiber optic bundle projects from the connector module 16 and is supported on a support member 32 at the second focus of the reflector 28. The fiber optic bundle 30 extends distally through the rigid insertion tube 12 and is fanned out around a miniature camera assembly 34 at the distal tip 14 of the tube 12. The optical fibers are distributed in an arc or a ring, and they emit light from their distal ends through a glass face plate 36 at the end of the tube 12.

The camera 34 has a lens assembly 38 containing a set of focusing lenses 40 which focus an image of a target onto an image forming surface of a CCD imager 42 or other equivalent imager. A power and signal wiring harness 44 has conductors coupled to terminals of the imager 42, and extends proximally to the connector module 16.

A rotary color filter wheel 46 can be incorporated in the processor 20 at the light source 24. Because of the small spot size produced by the light source, the filter wheel can be made very small and light weight. The purpose of the wheel 46 is to produce sequential primary colors of light, and its operation is similar to that described in U.S. Pat. No. 4,523,224.

The bundle 30 is preferably formed of optical glass fibers, but because of the low amount of heat associated with the illumination, synthetic plastic optical fibers can be used if desired.

Also, while not shown here, plural light sources can be incorporated into the processor unit 20, and the optical fiber bundle 30 can be bifurcated so that either or both of the light sources can be employed with a given probe. This achieves a built-in back up illumination feature that permits an operation to proceed even in the event of lamp failure. Also, with plural lamps the illumination can be selected to be at higher or lower levels. It is also possible according to the principles of this invention, because of the low power requirements for the light sources and their associated ballasts and power supplies, to construct the processor unit 20 to accommodate several probes at once, each with an associated connector module 16, and each with a respective light source.

Figure 4:
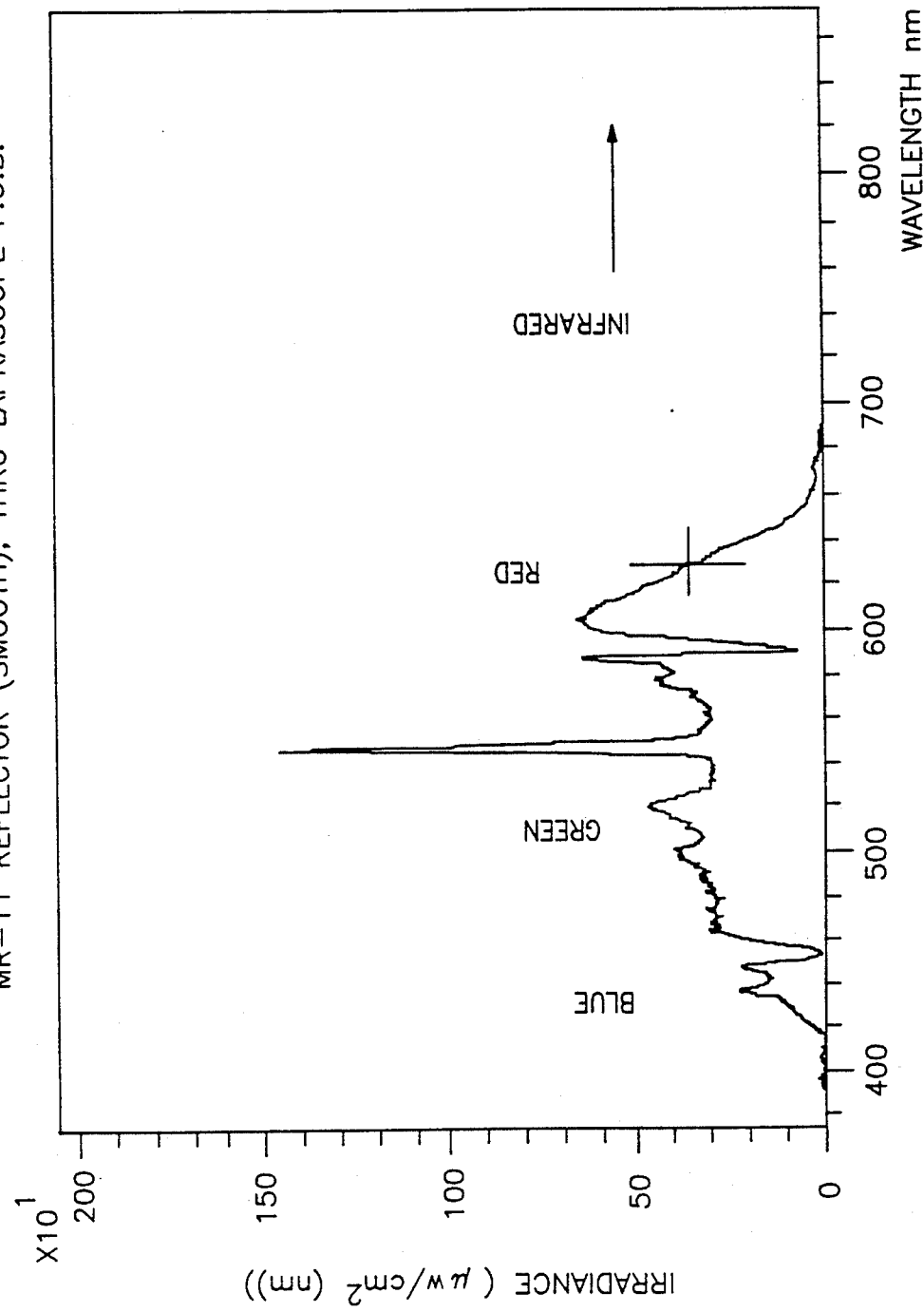
FIG. 4 is a chart of the light emission spectrum of a typical lamp as employed in the laparoscope of this invention.

The lamp 26 employed in the above described embodiment can give the emission spectrum as shown in FIG. 4. The lamp's output distribution is chosen to have balanced intensities of light in the red, green and blue portions of the visible spectrum. Although this spectrum appears rather jagged, both the human eye and the video camera will integrate the various wave lengths of each color, so the display on the color monitor 22 has life-like, true colors. This is important in helping the surgeon to recognize tissue conditions within a patient's body cavity because realistic color rendition makes the tissue easily recognizable.

Also as shown in FIG. 4, only a very small, inconsequential amount of radiation is generated in the infrared band.

While the invention has been described in detail with reference to a preferred embodiment, it should be recognized that the invention is not limited to that precise embodiment. Rather many modifications and variations will present themselves to those skilled in the art without departing from the scope and spirit of this invention as defined in the appended claims.

What is claimed is:

1. A video laparoscope which comprises an elongated insertion tube which includes a lens assembly for focussing light which enters a distal end of said insertion tube onto a miniature video imager which produces an image signal that represents a target located distally of the insertion tube, a video processor unit coupled to said insertion tube for processing said image signal and providing a video signal to a video monitor which reproduces an image of said target, and a light source providing illumination which is carried by a fiber optic bundle from said light source and through said insertion tube to its distal end from which the illumination is incident on said target, wherein said fiber optic bundle has a very small predetermined diameter;

wherein said light source includes a low-wattage metal halide discharge lamp with a power of about 20 to 50 watts and a small arc gap, which serves as a point source that produces white light comprised of red, green and blue wavelengths but does not produce appreciable amounts of infrared radiation, and ellipsoidal focussing reflector means for focusing the light produced by the lamp onto a small focal spot of a diameter of 0.1 inches or less at which a proximal end of the fiber optic bundle is disposed, the small spot matching the diameter of the fiber bundle so that substantially all of the light energy produced by the lamp and reflected from the reflector means is directed into the proximal end of the fiber bundle.

2. The video laparoscope of claim 1 wherein said focusing means includes an ellipsoidal reflector having said lamp situated at one focus and the proximal end of the fiber optic bundle situated at a second focus.

3. The video laparoscope of claim 1 wherein said lamp has a power of below about 50 watts.

4. The video laparoscope of claim 3 wherein said lamp power is about 20 watts.

5. The video laparoscope of claim 1 wherein said optical fiber bundle is formed of synthetic plastic optical fibers.

* * * * *